United States Patent [19]

Spengler et al.

[11] Patent Number: 4,885,078
[45] Date of Patent: Dec. 5, 1989

[54] DEVICES CAPABLE OF REMOVING SILICON AND ALUMINUM FROM GASEOUS ATMOSPHERES

[75] Inventors: Charles J. Spengler; Prabhakar Singh, both of Murrysville, Pa.

[73] Assignee: Westinghouse Electric Corp., Pittsburgh, Pa.

[21] Appl. No.: 280,911

[22] Filed: Dec. 7, 1988

[51] Int. Cl.⁴ .................. G01N 27/26; H01M 8/06
[52] U.S. Cl. .................. 204/432; 204/1 T; 429/31; 429/40
[58] Field of Search ............ 429/19, 30, 31, 33, 429/40; 204/1 T, 432

[56] References Cited

U.S. PATENT DOCUMENTS

| Re. 28,792 | 4/1976 | Ruka et al. | 204/1 T |
|---|---|---|---|
| 4,395,468 | 7/1983 | Isenberg | 429/31 |
| 4,490,444 | 12/1984 | Isenberg | 429/31 |
| 4,645,587 | 2/1987 | Kokayeff | 208/91 |
| 4,728,584 | 3/1988 | Isenberg | 429/31 |
| 4,767,518 | 8/1988 | Maskalick | 429/40 |

Primary Examiner—Donald L. Walton
Attorney, Agent, or Firm—Daniel P. Cillo

[57] ABSTRACT

An electrochemical device is made of a containment vessel (30) optional ceramic material within the containment vessel and including one or more electrochemical cells (10), the cells containing a porous exposed electrode (11) in contact with a solid electrolyte, where at least one of the exposed electrode, the containment vessel, and the optional ceramic material contains a deposit selected from metal oxide and metal salt capable of forming a metal oxide upon heating, where the metal is selected from the group consisting of Ce, Sm, Mg, Be, Ca, Sr, Ti, Zr, Hf, Y, La, Pr, Nb, Pm, Eu, Gd, Tb, Dy, Ho, Er, Tm, Yb, Lu, Th, U, and their mixtures.

12 Claims, 2 Drawing Sheets

DEVICES CAPABLE OF REMOVING SILICON AND ALUMINUM FROM GASEOUS ATMOSPHERES

GOVERNMENT CONTRACT

The Government of the U.S. of America has rights in this invention pursuant to contract No. DE-AC-2180ET-17089 awarded by the U.S. Department of Energy.

BACKGROUND OF THE INVENTION

1. Field of the Invention

The present invention relates to electrochemical devices such as solid electrolyte fuel cells and solid electrolyte gas sensors operating in a silicon and/or aluminum containing gaseous atmosphere.

2. Description of the Prior Art

High temperature solid oxide electrolyte fuel cells convert chemical energy into direct current electrical energy, typically at temperatures of from about 800° C. to 1200° C. Such solid oxide fuel cells are well known, and taught, for example, by Isenberg in U.S. Pat. Nos. 4,395,468 and 4,490,444. In these patents, an axially elongated, tubular, porous air cathode, usually made of a doped oxide of the perovskite family, for example doped or undoped lanthanum manganite, $LaMnO_3$, has a gas impervious solid oxide electrolyte deposited over it, except for a small radial segment which contains a deposit of interconnection material down the length of the tube. The solid oxide electrolyte is usually stabilized zirconia, for example $(ZrO_2)_{.9}(Y_2O_3)_{.1}$. A porous fuel electrode, usually a nickel-zirconia cermet, forms an outer layer over the electrolyte, to provide a fuel cell. A metal fiber, current collector is then attached to the interconnection. Other solid oxide electrolyte fuel cell configurations are also known, such as those taught by Isenberg, in U.S. Pat. No. 4,728,584.

Another type of device utilizing a solid electrolyte is a gas sensor having electrolyte compositions uniquely responsive to $O_2$ gas, for example, electrolytes of yttria or calcia stabilized zirconia. These sensors are electrochemical concentration cells which sense the equilibrium of a gas species of interest and generate an electromotive force signal corresponding to the difference in partial pressure of the gas species across the solid electrolyte sensor. Typically, the solid state sensor includes an ion conductive solid electrolyte, with a lanthanum nickel oxide, nickel-platinum, or other type sensing and reference electrodes, disposed on its opposite surfaces. The stack gas, or monitored gas stream, contacts a sensing electrode, while the opposite electrode serves as a reference electrode which is contacted with a reference gas stream. These types of gas sensor devices operate at temperatures of between 600° C. and 1000° C., so that the solid electrolyte will exhibit the desired ion conductivity to generate a suitable electromotive force signal. Such devices are taught, for example, by Ruka et al., in U.S. Pat. Reissue No. 28,792.

In both the solid oxide electrolyte fuel cell and the solid electrolyte gas sensor, gases will contact both electrodes, which electrodes are disposed on opposite sides of the electrolyte. The gas medium contacting the fuel electrode of the fuel cell, and the sensing electrode of the gas sensor, may contain a wide variety of gases, including water vapor, and a wide variety of impurity materials. During operation of these devices silicon and aluminum containing gas species present as impurities in the gas medium can form deposits, and react with, the anode or sensing electrode and other components of the device, resulting in lower electrical performance and cell component degradation.

Once deposited as silica and alumina compounds, they cannot be removed effectively, and hence, the anode or sensing electrode surfaces become increasingly covered and encapsulated, and performance degradation becomes irreversible. The deposit of silicon and aluminum containing gas species, is promoted by low oxygen partial pressures and any water vapor present in the gas medium, and derives from impurities present in the containment material and/or from the thermal insulation materials used as part of the high temperature gas sensor system and high temperature fuel cell generator apparatus. The silicon and aluminum containing gas species may exist in a form of oxides and hydroxides such as SiO; $Si(OH)_2$; $SiO_2.nH_2O$; AlO; $Al(OH)_2$; and the like.

Kokayeff, in U.S. Pat. No. 4,645,587, recognized problems of Si and S contamination of reforming catalysts particularly those comprising platinum and rhenium. Kokayeff suggested passing Si and S containing hydrocarbon streams through a sorbent, comprising CuO and $Al_2O_3$, in the presence of molecular hydrogen, at over about 230° C. After silicon sorption, sulfur components in the effluent gas are removed in a hydrotreater containing a hydrotreating metal catalyst selected from mixture of Group VIII and Group VI B hydrogenation metal components, in possible combination with a phosphorus component. Preferred sulfur hydrotreating catalysts are nickel or cobalt mixed with molybdenum or tungsten. This process however, involves a complicated series of gas processing steps and does not remove aluminum containing species from the gas.

What is needed, is an in-situ means to: (1) prevent silica and alumina formation on and encapsulation of the electrodes of electrochemical cells as in fuel cells and gas sensors, where such electrodes are in contact with a gaseous medium comprising silicon and aluminum containing gaseous species, and (2) prevent silicon and aluminum from reaching the electrodes by interspersing a suitably treated, inert, porous media in the gas stream path, where the gas is constrained to pass through the openings within the inert, porous media. It is an object of this invention to provide such means.

SUMMARY OF THE INVENTION

With the above objects in mind, the present invention resides, generally, in an electrochemical device comprising a containment vessel and optional ceramic material within the containment vessel and including at least one electrochemical cell, the cell comprising a porous, exposed electrode, in contact with a solid electrolyte, characterized in that at least one of the exposed electrode, the containment vessel, and the optional ceramic material within the containment vessel, contains a deposit selected from metal oxide and metal salt capable of forming metal oxide upon heating, where the metal is selected from the group consisting of Ce, Sm, Mg, Be, Ca, Sr, Ti, Zr, Hf, Y, La, Pr, Nb, Pm, Eu, Gd, Tb, Dy, Ho, Er, Tm, Yb, Lu, Th, U, and mixtures thereof. Appropriate salts would include, preferably, nitrates, formates, acetates, propionates and butyrates. The term "exposed electrode", as used herein, means that electrode of the fuel cell or gas sensor that is contacted with fuel gas or monitored gas respectively, i.e., the fuel electrode of the fuel cell or the gas sensing electrode of the gas sensor, both of which are external electrodes.

The electrochemical cell can be a fuel cell, which preferably contains an attached nickel fiber current collector felt, and the exposed fuel electrode and current collector felt are impregnated with the deposit of metal salt. The electrochemical cell can also be a high temperature gas sensor, such as an $O_2$ sensor, where the exposed gas sensing electrode is impregnated with the deposit of metal salt, or coated with a porous layer of the metal oxide. Insulation materials and support or other type ceramic media within the containment vessel and the containment vessel itself can also be impregnated or coated according to this invention. Metal salts which would form compositions harmful to the electrochemical cell upon heating, such as carbonates and the like, must be excluded.

The preferred method of applying the metal salt is by vacuum impregnation. Preferably, the electrode is completely impregnated, and upon heating, minute metal oxides particles form not only on the electrode, but also near the electrochemical zone deep within the electrode at the solid electrolyte interface. The preferred method of applying the metal oxide to the electrode surface is by plasma spray techniques. These oxides are effective to prevent cell deterioration due to $SiO_2$ and $Al_2O_3$ deposition from the gas feed.

BRIEF DESCRIPTION OF THE DRAWINGS

The invention will become more readily apparent from the following description o certain embodiments thereof shown, by way of example only, in the accompanying drawings in which.

DESCRIPTION OF THE PREFERRED EMBODIMENTS

Figure 1:
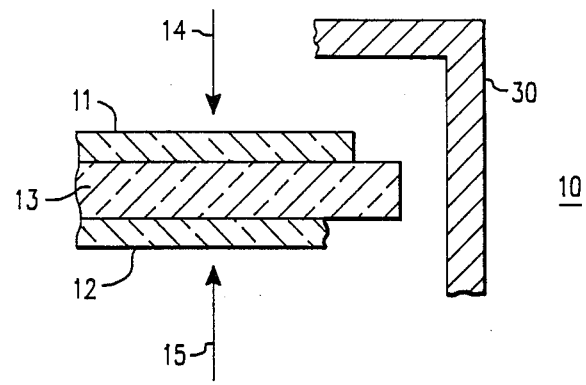
FIG. 1, which best illustrates the concept of the invention, is a cross-sectional view of an electrochemical device having gas contacting electrodes also in contact with a solid electrolyte.

Referring now to FIG. 1 of the drawings, a fragmented cross-section of an electrochemical cell 10 is shown, with an exposed, first, gas contacting electrode 11, and an interior, second, gas contacting electrode 12, where both electrodes are also in contact with a solid electrolyte 13 disposed therebetween. The solid electrolyte is ion permeable at high temperatures. A first gas 14 is shown by an arrow as contacting the first electrode 11, and a second gas 15 is shown by another arrow as contacting the second electrode 12. A fragmented section of a containment vessel 30 is also shown. Optional ceramic insulation and the like within the containment vessel is not shown.

When the electrochemical cell is a fuel cell, the exposed first electrode 11 will be a fuel electrode in contact with a gaseous fuel 14, such as hydrogen, carbon monoxide, or methane, which may also contain water vapor and a variety of silicon and aluminum containing gas species. The second electrode 12 will be an air electrode in contact with a source of oxygen, and the electrolyte will be a solid oxide electrolyte which is oxygen ion permeable at high temperatures.

When the electrochemical cell is a gas sensor, the exposed first electrode 11 will be the sensing electrode in contact with the monitored gas environment 14, containing the gas species, of interest, for example a monitored exhaust or flue gas containing $O_2$ species. The second electrode 12 will be a reference electrode in contact with a reference gas 15. In the example given above, the reference gas source would contain a stable or known concentration of $O_2$. The electrolyte would be a solid material which is oxygen ion permeable and could be made of stabilized zirconia. Other type gas sensors, which contain a solid, internal material which decomposes upon heating to provide a reference gas source, and which contain sensing electrodes exposed to a monitored gas environment, can also be impregnated according to this invention.

Figure 2:
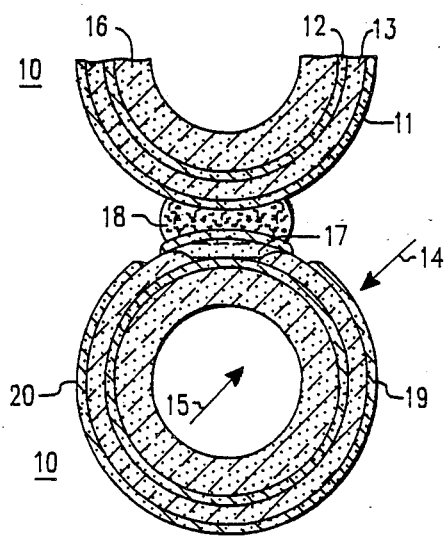
FIG. 2 is a cross-sectional view of two tubular fuel cells connected in series through a metal fiber current collector felt.

One cross-sectional configuration of an axially elongated, tubular, solid oxide electrolyte fuel cell is shown in FIG. 2. Since this is the preferred type of electrochemical device according to this invention, it will be described in detail. Each cell 10 may include an optional, porous support tube 16 of, for example, calcia stabilized zirconia. The air electrode cathode 12 is porous and can be made of doped oxides of the perovskite family, such as $CaMnO_3$, $LaNiO_3$, $LaCoO_3$, $LaCrO_3$, $In_2O_3$, and preferably $LaMnO_3$. Preferred dopants are strontium, calcium, cobalt, nickel, iron, and tin. Gas tight solid electrolyte 13, usually yttria stabilized zirconia surrounds the outer periphery of the air electrode. However, a selected radial segment is masked during electrolyte deposition, and a layer of interconnection material 17 is deposited on this segment. This interconnection extends along the active length of each elongated cell. The preferred interconnection is lanthanum chromite doped with calcium, strontium or magnesium.

Substantially surrounding the solid electrolyte 13 is a porous fuel electrode anode 11, of, for example, a nickel-zirconia or cobalt-zirconia cermet. As shown, the anode 11 is also discontinuous, being spaced from the interconnection 17 a distance sufficient to avoid direct electrical communication between the anode 11 and the interconnection 17 and the cathode 12. FIG. 2 also shows the series interconnection between consecutive fuel cells 10. The electrical interconnection is preferably enhanced by a metal felt 18 made, for example, of nickel fibers. The felt extends axially between the annular cells 10, and is bonded to each by pressure contact which causes sinter bonding during operation.

During operation of the fuel cell, air, or oxygen 15 flows through the center of the annular cells 10, and fuel 14 passes over the exterior. Oxygen molecules diffuse through the porous cathode 12. Fuel diffuses through the anode 11. Oxygen ions pass through the electrolyte 13. These reactants electrochemically interact at the interface between the electrolyte and the anode, generating products such as water vapor and carbon dioxide, as well as heat and electrical energy. Electrical power is transferred in series from the inner cathode 12 of one cell to the outer anode 11 of the next cell. The electrical power is usefully drawn through leads not shown. Additional metal fiber current collector felts may be attached as at points 19 and 20 to provide parallel connections to additional side by side cells of a fuel cell bundle, not shown in FIG. 2.

Figure 3:
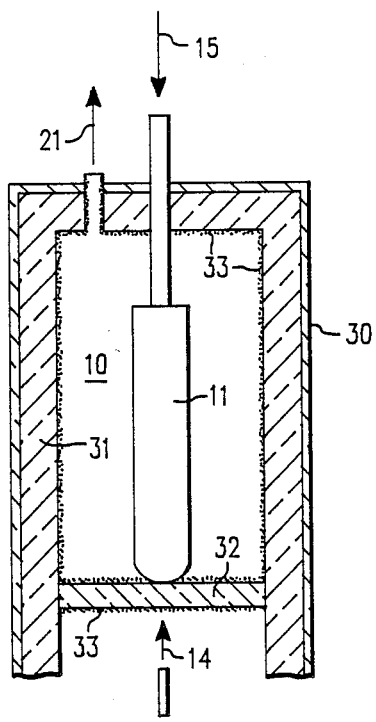
FIG. 3 is a cross-sectional view of a simple fuel cell.

Referring to FIG. 3, an electrochemical cell 10 such as a fuel cell, is shown, having exposed fuel electrode 11, all within a metal containment vessel 30. The fuel cell 10 can be of the same type shown in FIG. 2. Within the containment vessel 30, there can be a wide variety of internal, porous, ceramic material, such as alumina insulation 31 and structural member 32, which, in addition to the electrode 11, may contain a deposit of metal oxide, or in the case of a fuel cell, most likely a deposit of metal salt, shown grossly magnified as 33. Gaseous fuel is shown as arrow 14, oxidant as arrow 15 and exhaust gas as arrow 21.

Figure 4:
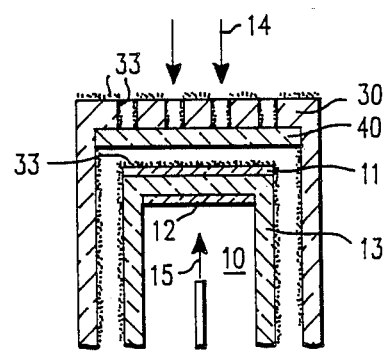
FIG. 4 is a cross-sectional view of a simple gas sensor.

FIG. 4 shows a gas sensor type of electrochemical cell 10, having exposed sensing electrode 11, which may consist of a platinum or other metal layer, oxygen ion conducting solid electrolyte, such as yttria or calcia stabilized zirconia 13, and monitor electrode 12, all within a containment vessel 30, such as a metal sheath or the ceramic material shown. Within the containment vessel a wide variety of internal, ceramic, porous media may be used, such as support 40. Gas to be monitored is shown as arrow 14 and reference gas as arrow 15. The containment vessel 30, structural member 40, the surface of the sensing electrode and even the electrolyte 13 may contain a deposit of metal salt, or in the case of a gas sensor, most likely a deposit of metal oxide, shown grossly magnified as 33. Utilization of a coated or impregnated ceramic, media barrier, such as member 32 in FIG. 3 and member 40 in FIG. 4, between the exposed electrode of the electrochemical cell and any contaminated gas fed through the gas feed entrance can be particularly advantageous in reducing Si and Al contamination. It is to be recognized that FIGS. 3 and 4 illustrate only very basic types of electrochemical cells.

A plurality of assembled fuel cells, i.e., a fuel cell bundle, or individual fuel cells, or gas sensor cells as such or with associated probe structure, heating element, and the like, here all considered an "electrochemical device" can be impregnated or coated according to this invention. The impregnation method is characterized by first applying a metal salt capable of forming a metal oxide upon heating, to the exterior surface of the electrochemical device which contains the exposed gas contacting electrode, or to the containment vessel or internal ceramic material. In the case of fuel cells the configuration of the cells can be round, oval, flattened, triangular, and the like, and can be of single elongated construction, a plurality of separate cell segments on a cell assembly, or a monolithic corrugated construction. In case of the internal ceramic material, the configuration can be planar, cyclindrical or any convenient geometry that allows gas contact.

The metal salt is preferably selected from the group consisting of nitrates, formates, acetates, propionates, and butyrates. Phosphates and particularly sulfates can harm the electrochemical cell activity and are excluded even from the inert porous media. The metal is selected from the group consisting of Ce, Sm, Mg, Be, Ca, Sr, Ti, Zr, Hf, Y, La, Pr, Nb, Pm, Eu, Gd, Tb, Dy, Ho, Er, Tm, Yb, Lu, Th, U, and mixtures thereof. Metals such as Ca alone, Al alone, Ba, and the like may form compositions at 1000° C. in the presence of $H_2O$ and fuel that can be harmful to cell operation, and must be excluded. For example, Ba can form carbonates and hydroxides in a fuel environment at high temperatures that easily flake off surfaces and which can be carried by the fuel stream to deposit in undesirable locations elsewhere in the device.

In the case of impregnation, optionally, from 0.5 wt. % to 6 wt. % preferably 1 wt. % to 3 wt. %, based on metal salt weight, of a nonionic surface-active agent, i.e., nonionic surfactant, which reduces interfacial tension between the metal salt solution and the fuel electrode surface on the internal ceramic material, can be used. These types of materials are well known in the art and can include alkylaryl ether alcohols, alkylaryl polyether alcohols, alkylaryl polyethylene glycol ethers, and the like. Ionic surfactants, containing for example Na, K, etc., and anionic surfactants, containing, for example Cl, $PO_4$, etc., could contaminate the electrochemical cell after heat-up. These materials are not necessary but help in impregnation. Before application to the surface of the electrochemical cell containing the fuel electrode, the metal salt solution is de-aerated to remove trapped air, such as by heating for a short period.

Preferably, the metal salt solution is applied by vacuum impregnation techniques, where the electrochemical device, containment vessel or internal ceramic material is placed in a container and a vacuum is drawn. Then, the metal salt solution is added at atmospheric pressure or at an applied pressure. This removes substantially all of the trapped air and helps promote complete penetration of metal salt solution through the bulk of the electrode to the interface of the electrolyte. Pressurized spraying is also a useful application technique, dipping or brushing are less preferred but are also useful. After application, the metal salts are allowed to dry, preferably at approximately 25° C., to form a dried impregnated deposit.

In the case of fuel cells, single electrochemical cells impregnated in this fashion can then be made into a bundle. Preferably, the bundle itself, containing a plurality of electrically connected cells, also possibly including bus bars, is impregnated as one unit. The bundle, or other configuration of cells or inert, porous ceramic media as described previously, can then be placed into an electrochemical generator. Heated fuel is fed into the generator to reach start up temperature and then oxidant, such as air is also fed into the generator.

At operating temperatures of approximately 800° C. to 1000° C. the applied salts, in the fuel cell assembly in, for example an electrical generator, or in the gas sensor probe apparatus, will form oxides, for example MgO, $CeO_2$, $SmO_2$ or the like. These oxides are formed as minute particles approximately 0.01 micron to 1 micron in diameter. The outer most oxide particulates capture Si and Al so that little if any Si or Al gets through to approach the electrochemical zone near the electrolyte.

Upon vaporization of nitrate, formate, acetate, propionate and butyrate components of the salt, the coating, if it was not discontinuous after drying, will now become discontinuous, so that the electrode is exposed. These metal oxides are also distributed through the bulk of the fuel electrode and the internal inert, porous ceramic media. These metal oxides are capable of preferentially reacting with any Si or Al such as SiO; $Si(OH)_2$; $SiO_2.nH_2O$ $Al(OH)_2$; and the like, to form stable silicates or aluminates, and diminish $SiO_2$ and $Al_2O_3$ deposition on and within the exposed electrode.

The alternate, in-situ metal oxide coating method is particularly suitable for exposed electrodes used in gas sensors, where such electrodes are not overly porous and are very thin. Here, hot plasma spraying techniques, well known in the art, can be used to deposit the metal oxide directly on the desired surfaces. This requires no salt evaporation. As described previously, the metal oxides are capable of preferentially reacting with Si or Al to form stable silicates of aluminates and diminish $SiO_2$ and $Al_2O_3$ deposition. Again, the metal of the metal oxide is selected from the group consisting of Ce, Sm, Mg, Be, Ca, Sr, Ti, Zr, Hf, Y, La, Pr, Nb, Pm, Eu, Gd, Tb, Dy, Ho, Er, Tm, Yb, Lu, Th, U, and mixtures thereof. In both methods and for the deposits herein described the preferred metals are Ce, Sm and their mixtures. This invention is directed to gas streams containing Si and/or Al, rather than hydrocarbon gases.

The invention will now be illustrated by reference to the following non-limiting Example.

EXAMPLE

An axially elongated, electrochemical, solid oxide fuel cell, as depicted in FIG. 3, having a cross-section similar to those shown in FIG. 2 of the Drawings, was made. It had a calcia stabilized zirconia support tube, a lanthanum manganite interior air electrode, a yttria stabilized zirconia electrolyte, a nickel-stabilized zirconia cermet, exterior, exposed fuel electrode, where a yttria stabilized zirconia skeleton was grown around 5 micron nickel particles by a vapor deposition process well known in the art, and a magnesium doped lanthanum chromite interconnection. The cell tested favorably for leak tightness. It was about 40 cm long, with a 36 cm long active length, and 1.5 cm outside diameter.

The fuel cell was placed in a horizontally fixed long tubular closed end vessel having one end closure and a plurality of rubber septum side closures. A vacuum was drawn on the fuel cell. Then a degassed aqueous solution of research grade cerium-samarium nitrate solution containing about 0.013 g. (3 wt. %) nonionic surfactant was placed in a hypodermic needle. The metal salt solution was squirted onto a plurality of portions of the fuel cell by inserting the hypodermic through the rubber septums. The cell was left in the chamber for about 3 hours for soaking and uniform distribution of the metal salt solution. Impregnation by capillary action on the metal salt was visually apparent. The cell was later dried at 25° C. for 24 hours.

The cell was then installed in a cell test envelope made of alumina lined quartz for electrochemical evaluation. The cell temperature was slowly raised to 600° C. over 16 hours duration, in a 90% $N_2$-5% $H_2$-5% $H_2O$ atmosphere, to effect cell heat up. The cell was then brought up to and through 800° C., at which time magnesium oxides were formed on and in the impregnated Sample A cell. The cell was then operated at 1000° C. in 95% $H_2$-5% $H_2O$, to obtain stable cell voltage. Fuel was then changed to a 66.6% $H_2$, 22.2% CO, 11.1% $H_2O$ gas mixture, to simulate coal derived gas. This fuel contained silicon bearing gas species originating from a silica test envelope and impurities in the alumina test envelope.

Upon completion of about 300 hours operation the full cell was cut in cross-section and subjected to electron beam microanalysis. Polished sections of the fuel electrode disclosed that silicon had reacted with the cerium-samarium oxide phase preferentially, especially at the entrance points to the porous fuel electrode.

We claim:

1. An electrochemical device, comprising a containment vessel and optional ceramic material within the containment vessel and including at least one electrochemical cell, the cell comprising a porous, exposed electrode in contact with a solid electrolyte, the improvement characterized in that at least one of the exposed electrode, the containment vessel, and the optional material within the containment vessel, contains a deposit selected from metal oxide and metal salt capable of forming metal oxide upon heating, where the metal is selected from the group consisting of Ce, Sm, Mg, Be, Ca, Sr, Ti, Zr, Hf, Y, La, Pr, Nb, Pm, Eu, Gd, Tb, Dy, Ho, Er, Tm, Yb, Lu, Th, U, and mixtures thereof.

2. The electrochemical device of claim 1, where the electrochemical cell is a fuel cell, and comprises a porous exposed fuel electrode containing nickel, an air electrode, and a solid electrolyte therebetween.

3. The electrochemical device of claim 1, where the electrochemical cell is a gas sensor, and comprises a porous, exposed sensing electrode, a reference electrode, and a solid electrolyte therebetween.

4. The electrochemical device of claim 2, where the deposit is a metal salt which is impregnated through the bulk of the exposed electrode and through porous ceramic material within the containment vessel.

5. The electrochemical device of claim 2, where the deposit is a metal salt and the metal of the metal salt is selected from Ce, Sm and mixtures thereof.

6. The electrochemical device of claim 2, where the metal salt is a salt selected from the group consisting of nitrate, formate, acetate, propionate, butyrate, and mixtures thereof.

7. The electrochemical device of claim 2, where the deposit is a metal salt, the device can be operated in a gas feed which contacts the exposed electrode at a temperature of at least 800° C. to form metal oxides from the metal salts, which metal oxides are effective to prevent cell deterioration due to Si and Al deposition from the gas feed, and where a porous ceramic member impregnated with metal salt is disposed between the fuel cell and the gas feed entrance.

8. The electrochemical device of claim 2, where the electrochemical cell has a tubular, axially elongated configuration.

9. The electrochemical device of claim 2, where the device comprises a plurality of cells electrically connected together.

10. The electrochemical device of claim 3, where the deposit is a metal oxide which is coated on the surface of the exposed electrode and on ceramic material within the containment vessel.

11. The electrochemical device of claim 3, where the deposit is a metal oxide and the metal of the metal oxide is selected from Ce, Sm and mixtures thereof.

12. The electrochemical device of claim 3, where the deposit is a metal oxide, which contacts the exposed electrode, where the device can be operated in a gas feed which contacts the exposed electrode at a temperature of at least 800° C., which metal oxides are effective to prevent cell deterioration due to Si and Al deposition from the gas feed, and where a porous ceramic member coated with metal oxide is disposed between the gas sensor and the gas feed entrance.

* * * * *